United States Patent
Müller et al.

(10) Patent No.: US 10,538,809 B2
(45) Date of Patent: Jan. 21, 2020

(54) METHOD OF AMPLIFICATION OF A SHORT TANDEM REPEAT LOCUS

(71) Applicant: QIAGEN GMBH, Hilden (DE)

(72) Inventors: Daniel Müller, Hilden (DE); Sascha Strauss, Solingen (DE)

(73) Assignee: QIAGEN GMBH, Hilden (DE)

( * ) Notice: Subject to any disclaimer, the term of this patent is extended or adjusted under 35 U.S.C. 154(b) by 541 days.

(21) Appl. No.: 15/113,211

(22) PCT Filed: Jan. 28, 2015

(86) PCT No.: PCT/EP2015/051706
§ 371 (c)(1),
(2) Date: Jul. 21, 2016

(87) PCT Pub. No.: WO2015/114005
PCT Pub. Date: Aug. 6, 2015

(65) Prior Publication Data
US 2017/0009294 A1    Jan. 12, 2017

(30) Foreign Application Priority Data

Jan. 28, 2014  (EP) .................................... 14152841

(51) Int. Cl.
*C12Q 1/68* (2018.01)
*C12Q 1/6881* (2018.01)
*C12Q 1/686* (2018.01)

(52) U.S. Cl.
CPC .......... *C12Q 1/6881* (2013.01); *C12Q 1/686* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS 9,783,850 B2 * 10/2017 Frumkin .............. C12Q 1/6858

OTHER PUBLICATIONS

Davis et al (Forensic Sci Intl, 2012, vol. 6, p. 494-497) (Year: 2012).*
Scharff et al. (Blood et al., 1995, 85(7):1954-1963) (Year: 1995).*
Lowe et al. (Nucleic Acids Research, 1990, 18(7):1757-1761) (Year: 1990).*

* cited by examiner

*Primary Examiner* — Stephanie K Mummert
(74) *Attorney, Agent, or Firm* — Ballard Spahr LLP (57) ABSTRACT

Short tandem repeat (STR) markers are genetic elements that are frequently used in the fields of forensic analysis, paternity determination and detection of genetic diseases and cancers. Such analysis involves the amplification of STR loci. Technically, this can be challenging due to sequence variations in the flanking regions of the locus. In the case of SE33, previous amplification efforts have failed. The present invention describes a set of primers for the amplification of SE33 and a method for the analysis of the presence and/or level of SE33, also in combination with other STRs.

10 Claims, 4 Drawing Sheets
Specification includes a Sequence Listing.

SEQUENCE LISTING

```
<160> NUMBER OF SEQ ID NOS: 8

<210> SEQ ID NO 1
<211> LENGTH: 20
<212> TYPE: DNA
<213> ORGANISM: Homo sapiens

<400> SEQUENCE: 1
gaggctacag tgagccgagg                                               20

<210> SEQ ID NO 2
<211> LENGTH: 26
<212> TYPE: DNA
<213> ORGANISM: Homo sapiens

<400> SEQUENCE: 2
cgcggtgtaa ggaggtttat atatat                                        26

<210> SEQ ID NO 3
<211> LENGTH: 20
<212> TYPE: DNA
<213> ORGANISM: Homo sapiens

<400> SEQUENCE: 3
tacagtgagc cgaggtcatg                                               20

<210> SEQ ID NO 4
<211> LENGTH: 23
<212> TYPE: DNA
<213> ORGANISM: Homo sapiens

<400> SEQUENCE: 4
cgcggtgtaa ggaggtttat ata                                           23

<210> SEQ ID NO 5
<211> LENGTH: 20
<212> TYPE: DNA
<213> ORGANISM: Homo sapiens

<400> SEQUENCE: 5
gtgagccgag gtcatgccat                                               20

<210> SEQ ID NO 6
<211> LENGTH: 22
<212> TYPE: DNA
<213> ORGANISM: Homo sapiens

<400> SEQUENCE: 6
ctccgcggtg taaggaggtt ta                                            22

<210> SEQ ID NO 7
<211> LENGTH: 20
<212> TYPE: DNA
<213> ORGANISM: Homo sapiens

<400> SEQUENCE: 7
acatctcccc taccgctata                                               20
```

```
<210> SEQ ID NO 8
<211> LENGTH: 20
<212> TYPE: DNA
<213> ORGANISM: Homo sapiens

<400> SEQUENCE: 8
acagtgagcc gaggtcatgc                                              20
```

METHOD OF AMPLIFICATION OF A SHORT TANDEM REPEAT LOCUS

CROSS REFERENCE TO RELATED APPLICATIONS

This application is a national phase filing of International Patent Application No. PCT/EP2015/051706, filed Jan. 28, 2015, which claims priority to European Application No. 14152841.4, filed on Jan. 28, 2014, both of which are herein incorporated by reference in their entireties.

REFERENCE TO SEQUENCE LISTING

The Sequence Listing submitted Jul. 21, 2016, as a text file named "37578_0045U1_Sequence_Listing.txt," created on Jul. 19, 2016, and having a size of 1,464 bytes is hereby incorporated by reference pursuant to 37 C.F.R. § 1.52(e)(5).

FIELD OF THE INVENTION

Short tandem repeat (STR) markers are sequence motifs that consist of repeatedly occurring short sequences in non-coding parts of the genome. They are polymorphous with regard to the number of repeats which led during evolution to a high number of variants for every STR loci. Therefore, there is a high probability that two human beings differ in the number of STR repeats and therefore STR5 have been discovered and developed as genetic markers. Such markers are frequently used by scientists in the field of forensic analysis, paternity determination, monitoring of bone marrow transplantation, linkage mapping as well as detection of genetic diseases and different types of cancers.

Forensic investigations in Europe and in the United States involve a core loci set analysis. In order to ensure that a match between two samples of tissue is statistically significant, multiple polymorphic loci need to be analyzed. The workflow scheme is such that the STR marker is amplified in a PCR reaction. However, this is often not a trivial task due to several complications.

In the case of SE33, amplification has been proven to be difficult. Upstream of the SE33 marker region, a repetitive element is found. Multiple copies of this repetitive element are found in the genome and this complicates the design of SE33-specific primers. In addition to the repetitive element, several single nucleotide polymorphisms (SNPs) and insertions/deletions (InDels) are located in close proximity to the marker region. Such sequence variations in the binding sites of the primers affect specificity and thereby decrease or even abolish efficient amplification of the marker region. The presence of a SNP prevented amplification when using the primers reported by Polymeropoulos et al (Polymeropoulos et al., Nucleic Acids Res., 1992, 20, 1432). Further, mistyping occurred due to the presence of SNPs which cause a change in hairpin structure of the amplicon.

A system for the amplification of SE33 and efficient genotyping would provide an important contribution to the field of forensic science.

BRIEF DESCRIPTION OF THE INVENTION

The invention addresses the technical problem with a set of primers for the efficient amplification of SE33 and also describes a method for the analysis of the presence and/or level of SE33 in combination with other STR markers.

The invention relates to a nucleic acid consisting of a sequence selected from the group of, a) SEQ ID NO: 1 and,
b) a nucleic acid that is at least preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO: 1 and preferably 95% identical to SEQ ID NO: 1, wherein said nucleic acid that is preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO:1, preferably 95% identical to SEQ ID NO: 1 has at least 5, 4, 3, 2 or 1 terminal 3'-prime nucleotides that are identical to SEQ ID NO: 1 and, wherein, said nucleic acid may also optionally be 1 to 5 nucleotides shorter at its 5' end. Terminal (identical) herein meaning the last nucleotides at the 3' end.

The invention further relates to a nucleic acid consisting of a sequence selected from the group of, a) SEQ ID NO: 1 and,
b) a nucleic acid that is at least 70% identical to SEQ ID NO: 1, wherein said nucleic acid that is at least 70% identical to SEQ ID NO: 1 has at least 5, 4, 3, 2 or 1 terminal 3'-nucleotides that are identical to the 5, 4, 3, 2 or 1 terminal 3'nucleotides of SEQ ID NO: 1 and, wherein, said nucleic acid may also optionally be 1 to 5 nucleotides shorter or longer at its 5' end. Terminal (identical) herein meaning the last nucleotides at the 3' end.

The invention relates to the use of a nucleic acid as described above in a method for amplifying a fragment of SE33 of a preferred fragment size of 385-500 by (related to allele 42), more preferred 400-475 (related to allele 42), most preferred 425-445 bp (related to allele 42).

The invention also relates to a method for the detection of the presence and/or level of the SE33 marker comprising the following steps:

i. mixing a sample with two nucleic acid oligonucleotides, wherein one nucleic acid is a forward primer consisting of a sequence selected from the group of
  a) SEQ ID NO: 1 and,
  b) a nucleic acid that is at least preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO: 1 and preferably 95% identical to SEQ ID NO: 1,
  wherein said nucleic acid that is preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO:1, preferably 95% identical to SEQ ID NO: 1 has at least 5, 4, 3, 2 or 1 terminal 3'-prime nucleotides that are identical to SEQ ID NO: 1 and, wherein, said nucleic acid may also optionally be 1 to 5 nucleotides shorter or longer at its 5' end and
  the other is a reverse primer suitable to form an amplification product when used with said forward primer in an amplification reaction,
ii. performing an amplification reaction and
iii. detection of the presence and/or level of SE33.

The invention additionally relates to a method for the detection of the presence and/or level of the SE33 marker comprising the following steps:

i. mixing a sample with two nucleic acid oligonucleotides, wherein one nucleic acid is a forward primer consisting of a sequence selected from the group of a) SEQ ID NO: 1 and,
b) a nucleic acid that is at least 70% identical to SEQ ID NO: 1 wherein said nucleic acid that is at least 70% identical to SEQ ID NO: 1 has at least 5, 4, 3, 2 or 1 terminal 3'-nucleotides that are identical to the 5, 4, 3, 2 or 1 terminal 3'-nucleotides of SEQ ID NO: 1 and, wherein, said nucleic acid may also optionally be 1 to 5 nucleotides shorter or longer at its 5' end and the other is a reverse primer suitable to form an amplification product when used with said forward primer in an amplification reaction, ii. performing an amplification reaction and
iii. detection of the presence and/or level of SE33.

DETAILED DESCRIPTION OF THE INVENTION

The term "SE33" as used herein refers to the β-actin related pseudo gene. It is located on chromosome 6 (band 6q14), whereby about 83 allelic variants are known for SE33 to date. The GenBank accession number is AJ746167. The predominant repeat motif is AAAG, however the locus is highly polymorphic.

The term "amplification products" as used herein are nucleic acids or oligonucleotides that are the product of an amplification reaction, e.g. of a polymerase chain reaction. They are for example defined by the primers used for amplification.

An "oligonucleotide" herein refers to a stretch of nucleic acid, e.g. RNA or DNA, that comprises a sequence of two or more nucleotides, e.g. between 2 and 250 nucleotides, more preferably between 2 and 200, even more preferably between 2 and 100, even more preferably between 2 and 30, even more preferably between 2 and 25, even more preferably between 2 and 20, even more preferably between 5 and 25, and most preferably between 10 and 25 nucleotides.

A "primer" herein refers to an oligonucleotide comprising a sequence that is complementary to a nucleic acid to be amplified or transcribed ("template"). During replication polymerases attach nucleotides to the 3'-OH end of the primer complementary to the respective nucleotides of the template.

A "probe" herein is an oligonucleotide, nucleic acid or a fragment thereof, which is substantially complementary to a specific nucleic acid sequence.

The invention relates to a nucleic acid consisting of a sequence selected from the group of,
a) SEQ ID NO: 1 and,
b) a nucleic acid that is at least preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO: 1 and preferably 95% identical to SEQ ID NO: 1,
wherein said nucleic acid that is preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO:1, preferably 95% identical to SEQ ID NO: 1, has at least 5, 4, 3, 2 or 1 terminal 3'-prime nucleotides that are identical to SEQ ID NO: 1 and, wherein, said nucleic acid may also optionally be 1 to 5 nucleotides shorter or longer at its 5' end. Terminal, herein meaning the last nucleotides at the 3' end. Hence, if 5 are identical, these are the last 5, if 4 are identical these are the last 4 and so on.

The invention additionally relates to a nucleic acid consisting of a sequence selected from the group of,
a) SEQ ID NO: 1 and,
b) a nucleic acid that is at least 70% identical to SEQ ID NO: 1
wherein said nucleic acid that is at least 70% identical to SEQ ID NO: 1 has at least 5, 4, 3, 2 or 1 terminal 3'-nucleotides that are identical to the 5, 4, 3, 2 or 1 terminal 3'-nucleotides of SEQ ID NO: 1 and, wherein, said nucleic acid may also optionally be 1 to 5 nucleotides shorter or longer at its 5' end. Terminal, herein meaning the last nucleotides at the 3' end. Hence, if 5 are identical, these are the last 5, if 4 are identical these are the last 4 and so on.

In a preferred embodiment of the invention said nucleic acid is at least 75% identical to SEQ ID NO 1. In a more preferred embodiment of the invention said nucleic acid is at least 80% identical, more preferably 85% identical, even more preferably 90% identical and most preferably 95% identical to SEQ ID NO 1.

In a preferred embodiment the invention relates to a nucleic acid as described above, wherein the nucleic acid is a probe or primer.

In one embodiment of the invention the nucleic acid is a nucleic acid as describe above with a length of at the most 25 nucleotides. In a preferred embodiment the nucleic acid has a length of at the most 20 nucleotides. In another embodiment the nucleic acid has a length of 15 nucleotides or less.

In one embodiment the invention relates to a nucleic acid, wherein said nucleic acid may have a fluorescent dye attached and preferably, said dye is attached to the 5'-end of the nucleic acid.

The invention relates to the use of a nucleic acid as described above in a method for amplifying a fragment of SE33 of a preferred fragment size of 385-500 bp (related to allele 42), more preferred 400-475 (related to allele 42), most preferred 425-445 bp (related to allele 42).

The invention also relates to a method for the detection of the presence and/or level of the SE33 marker comprising the following steps:

i. mixing a sample with two nucleic acid oligonucleotides, wherein one nucleic acid is a forward primer consisting of a sequence selected from the group of
a) SEQ ID NO: 1 and,
b) a nucleic acid that is at least preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO: 1 and preferably 95% identical to SEQ ID NO: 1,
wherein said nucleic acid that is preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO:1, preferably 95% identical to SEQ ID NO: 1, has at least 5, 4, 3, 2 or 1 terminal 3'-prime nucleotides that are identical to SEQ ID NO: 1 and, wherein, said nucleic acid may also optionally be 1 to 5 nucleotides shorter or longer at its 5' end and
the other is a reverse primer suitable to form an amplification product when used with said forward primer in an amplification reaction, ii. performing an amplification reaction and
iii. detection of the presence and/or level of SE33.

The invention also relates to a method for the detection of the presence and/or level of the SE33 marker comprising the following steps:

i. mixing a sample with two nucleic acid oligonucleotides, wherein one nucleic acid is a forward primer consisting of a sequence selected from the group of
   a) SEQ ID NO: 1 and,
   b) a nucleic acid that is at least 70% identical to SEQ ID NO: 1 wherein said nucleic acid that is at least 70% identical to SEQ ID NO: 1 has at least 5, 4, 3, 2 or 1 terminal 3'-prime nucleotides that are identical to the 5, 4, 3, 2 or 1 3'-terminal nucleotides of SEQ ID NO: 1 and, wherein, said nucleic acid may also optionally be 1 to 5 nucleotides shorter or longer at its 5' end and
   the other is a reverse primer suitable to form an amplification product when used with said forward primer in an amplification reaction,
ii. performing an amplification reaction and
iii. detection of the presence and/or level of SE33.

In a preferred embodiment of the invention said forward primer is at least 75% identical to SEQ ID NO 1. In a more preferred embodiment of the invention said nucleic acid is at least 80% identical, more preferably 85% identical, even more preferably 90% identical and most preferably 95% identical to SEQ ID NO 1.

In one embodiment of the invention the nucleic acid is a nucleic acid as describe above with a length of at the most 25 nucleotides. In a preferred embodiment the nucleic acid has a length of at the most 20 nucleotides. In another embodiment the nucleic acid has a length of 15 nucleotides or less.

In one embodiment the invention relates to a method for the detection of the presence and/or level of the SE33 marker, wherein the reverse primer has a sequence selected from the group of SEQ ID NO: 2, SEQ ID NO: 4, SEQ ID NO: 6 and SEQ ID NO: 7.

In one embodiment the invention relates to a method, wherein the amplification is performed by using a method selected from the group polymerase chain reaction, rolling circle amplification, strand displacement amplification, transcription-based amplification system, nucleic acid sequence based amplification (NASBA), rolling circle amplification (RCA), transcription-mediated amplification (TMA), self-sustaining sequence replication (3SR), Qβ amplification, ligase chain reaction and isothermal amplification.

In a preferred embodiment the invention relates to a method, wherein the detection of the presence and/or level of SE33 is performed by a method selected from the group comprising capillary electrophoresis, qPCR, digital PCR, agarose gel electrophoresis and next generation sequencing. Such analysis of the amplification reaction gives further insights into quality of the reaction by analysis of the presence and/or quantity of the target product and for the presence of non-specific side products. Detection can be performed by means of fluorescence in the case labelled primers are used. Other options include agarose gel electrophoresis and subsequent analysis of the pattern of bands.

The invention also relates to a method, wherein the sample is genomic DNA.

In particular, the invention relates to a method, wherein the sample is from one of the following sources but not limited to: saliva, urine, faeces, semen, blood, blood serum, hair, skin, teeth, humerus and femur.

The invention preferably relates to a method, wherein the analysis of the SE33 marker is in the context of forensic science. The polymorphic STR markers D1S1656, D2S441, D2S1338, D3S1358, D5S818, D7S820, D8S1179, D10S1248, D12S391, D13S317, D16S539, D18S51, D19S433, D21S11, D22S1045, CSF1PO, FGA [FIBRA], TH01 [TC11], TPDX, vWA, SE33 [ACTBP2], DYS391 and the gender-specific Amelogenin marker, recommended by the CODIS (Combined DNA Index System) Core Loci Working Group, the European Network of Forensic Science Institutes (ENFSI) and the European DNA Profiling Group (EDNAP), are preferably used in the context of forensic science.

The invention relates to a method, wherein the presence and/or level of SE33 is analyzed in combination with other STR markers. The analysis of multiple STR markers in a sample ensures that the results obtained are statistically significant. Such analysis reduces the likelihood of random matches within the general population.

The invention relates to a method, wherein the analysis is performed using multiplex PCR.

In a preferred embodiment invention relates to a method, wherein the multiplex PCR comprises other STR markers selected from the group of D1S1656, D2S441, D2S1338, D3S1358, D5S818, D7S820, D8S1179, D10S1248, D12S391, D13S317, D16S539, D18S51, D19S433, D21S11, D22S1045, CSF1PO, FGA [FIBRA], TH01 [TC11], TPDX, vWA, SE33 [ACTBP2], DYS391 and the gender-specific Amelogenin marker.

In a preferred embodiment the invention relates to a method, wherein the multiplex PCR comprises other STR markers selected from the group of D1S1656, D2S441, D2S1338, D3S1358, D5S818, D7S820, D8S1179, D10S1248, D12S391, D13S317, D16S539, D18S51, D19S433, D21S11, D22S1045, CSF1PO, FGA [FIBRA], TH01 [TC11], TPDX, vWA, DYS391 and the gender-specific Amelogenin marker.

The invention relates to a kit for the detection of the SE33 marker in a sample comprising at least a nucleic acid, consisting of a sequence selected from the group of,
   a) SEQ ID NO: 1 and,
   b) a nucleic acid that is at least preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO: 1 and preferably 95% identical to SEQ ID NO: 1,
   wherein said nucleic acid that is preferably 70% identical to SEQ ID NO: 1, 75% identical to SEQ ID NO: 1, 80% identical to SEQ ID NO: 1, 85% identical to SEQ ID NO: 1, preferably 90% identical to SEQ ID NO:1 and preferably 95% identical to SEQ ID NO: 1 has at least 5, 4, 3, 2, 1 terminal 3'-prime nucleotides that are identical to SEQ ID NO: 1 and, wherein, said nucleic acid may also optionally be 1 to 5 nucleotides shorter or longer at its 5' end and reagents for amplification, detection and quantification of nucleic acids.

The invention further relates to a kit for the detection of the SE33 marker in a sample comprising at least a nucleic acid, consisting of a sequence selected from the group of,
   a) SEQ ID NO: 1 and,
   b) a nucleic acid that is at least 70% identical to SEQ ID NO: 1
wherein said nucleic acid that is at least 70% identical to SEQ ID NO: 1 has at least 5, 4, 3, 2, 1 terminal 3'-nucleotides that are identical to the 5, 4, 3, 2 or 1 terminal 3'-nucleotides of SEQ ID NO: 1 and, wherein, said nucleic acid may also optionally be 1 to 5 nucleotides shorter at its 5' end and reagents for amplification, detection and quantification of nucleic acids.

In a preferred embodiment of the invention said nucleic acid is at least 75% identical to SEQ ID NO 1. In a more preferred embodiment of the invention said nucleic acid is at least 80% identical, more preferably 85% identical, even more preferably 90% identical and most preferably 95% identical to SEQ ID NO 1.

In one embodiment of the invention the nucleic acid is a nucleic acid as describe above with a length of at the most 25 nucleotides. In a preferred embodiment the nucleic acid has a length of at the most 20 nucleotides. In another embodiment the nucleic acid has a length of 15 nucleotides or less.

In one embodiment the invention relates to a nucleic acid, wherein said nucleic acid may have a fluorescent dye attached and preferably, said dye is attached to the 5'-end of the nucleic acid.

EXAMPLES

Analysis of the SE33 Marker Region and Primer Design

Figure 1:
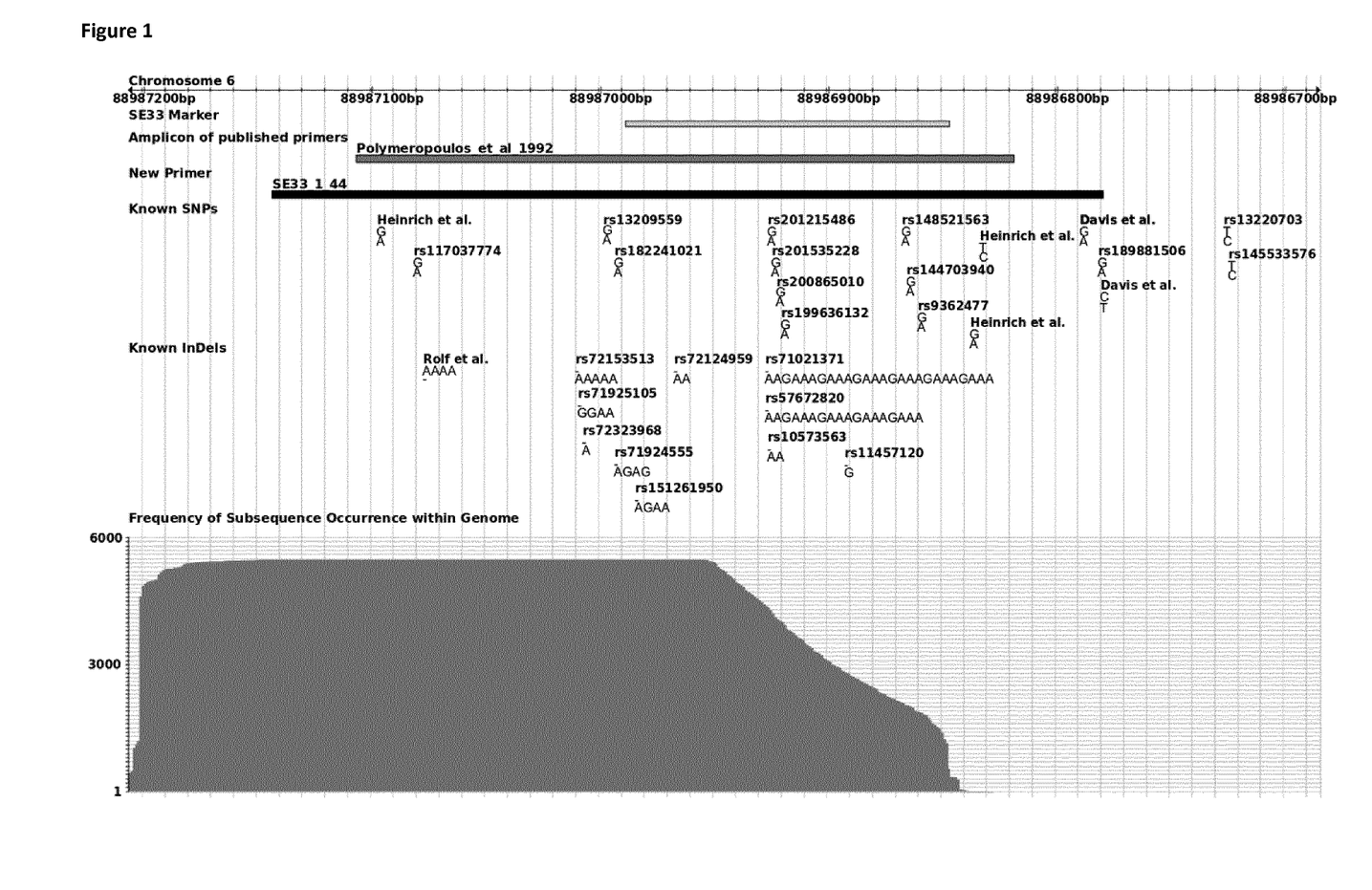

SE33 is located in a region of the human genome that makes the design of reliably working PCR primers difficult (FIG. 1).

A reliable and specific amplification of the SE33 marker was not possible with existing primers. Several reported mutations in the primer binding site lead to allelic dropouts or mistyping while determining the genotype of certain individuals. Specifically, the primers reported by Polymeropoulos et al. do not achieve the desired performance in the presence of SNP alleles as reported by Heinrich et al (Heinrich et al., International Journal of Legal Medicine, 2004, 118, 361-363). This leads to mistyping and misinterpretation of individual genotypes. Further, mistyping is observed in the presence of SNP alleles downstream of the SE33 marker, due to a change in a hairpin structure of the amplicon that leads to unwanted effects during the downstream analysis. For details, see Davis et al. (Davis et al., Forensic Science International: Genetics, 2012, 6, 494-497). In order to circumvent the mentioned issues, new PCR primers needed to be designed. However, the presence of a highly repetitive element upstream of the SE33 locus makes the design of specific primers difficult.

A set of primers was identified that is suited to amplify the SE33 locus with high specificity which are also robust to the presence of known mutations in a sample.

The size of the amplicon is compatible for a multiplex setup that allows the analysis of several other STR markers in a single reaction. These primers are listed in Table 1.

TABLE 1

Primers for the amplification of SE33.

| SEQ ID NO | Primer name | Sequence |
|---|---|---|
| 1 | SE33_1_44-F | GAGGCTACAGTGAGCCGAGG |
| 2 | SE33_1_44-R | CGCGGTGTAAGGAGGTTTATATATAT |
| 3 | SE33_1_22-F | TACAGTGAGCCGAGGTCATG |
| 4 | SE33_1_22-R | CGCGGTGTAAGGAGGTTTATATA |
| 5 | SE33_1_62-F | GTGAGCCGAGGTCATGCCAT |
| 6 | SE33_1_62-R | CTCCGCGGTGTAAGGAGGTTTA |
| 7 | SE33_1_P-R | ACATCTCCCCTACCGCTATA |

Multiplex PCR Experiments

In order to test the specificity of the primers and to assess their suitability for analysis of the SE33 locus in combination of other STR5, Multiplex PCR experiments were performed.

Figure 2:
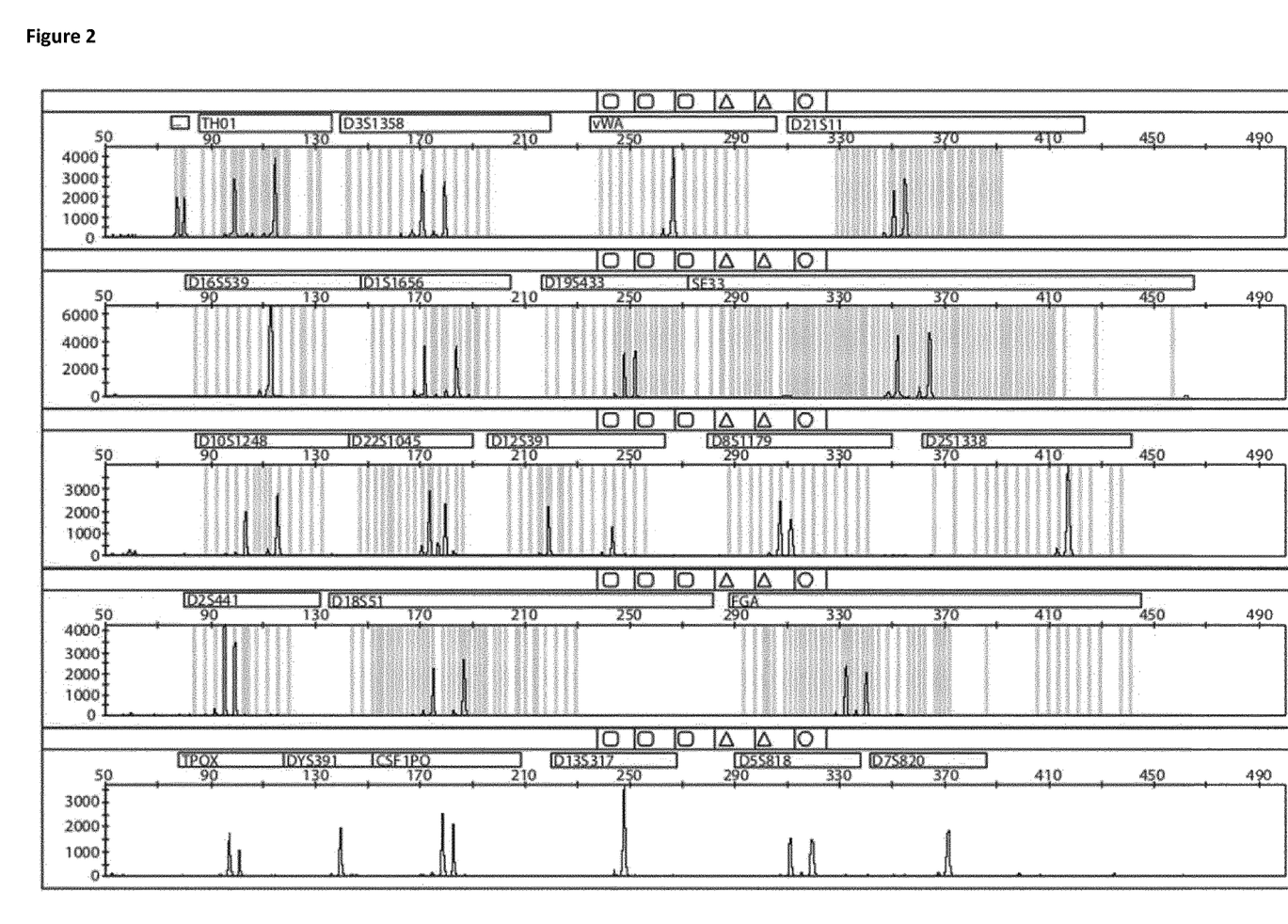

A Multiplex-PCR using 23 primer pairs simultaneously, including beside others the primer "SE33_1_44-F" (SEQ ID NO: 1) to amplify a fragment of the SE33 marker region was performed and the results are shown in FIG. 2. The amplified DNA fragments were analyzed with capillary electrophoresis (CE) on an ABI 3500 instrument. As seen in the electropherogram of the CE, all markers, in particular SE33, were amplified with a high and equal PCR yield. No unspecific products were detected. Therefore, this primer is suited for the simultaneous amplification of SE33 in parallel with 22 additional HuID markers.

Figure 3:
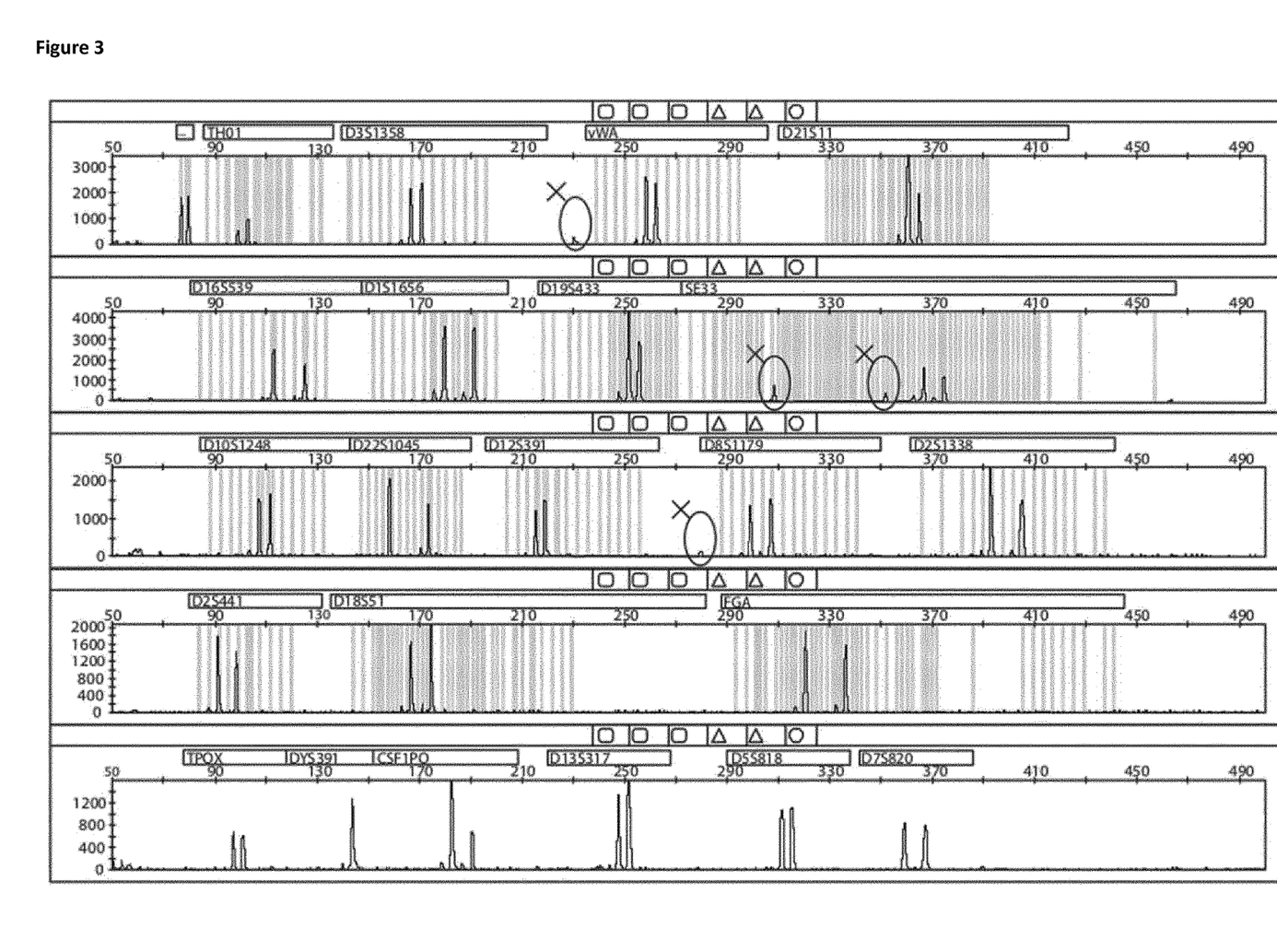

A multiplex PCR using 23 primer pairs simultaneously, including the primer pair "SE33_1_62-F//SE33_1_62-R" to amplify a fragment of the SE33 marker region is shown in FIG. 3. The amplified DNA fragments were analyzed with capillary electrophoresis (CE) on an ABI 3500 instrument. As seen in the electropherogram of the CE, the signal intensity of the SE33 PCR product is less than the signal intensities of the other markers. Furthermore, unspecific PCR products were detected in the blue, green and yellow channel. This highlights the complexity of designing an appropriate primer pair for SE33.

Figure 4:
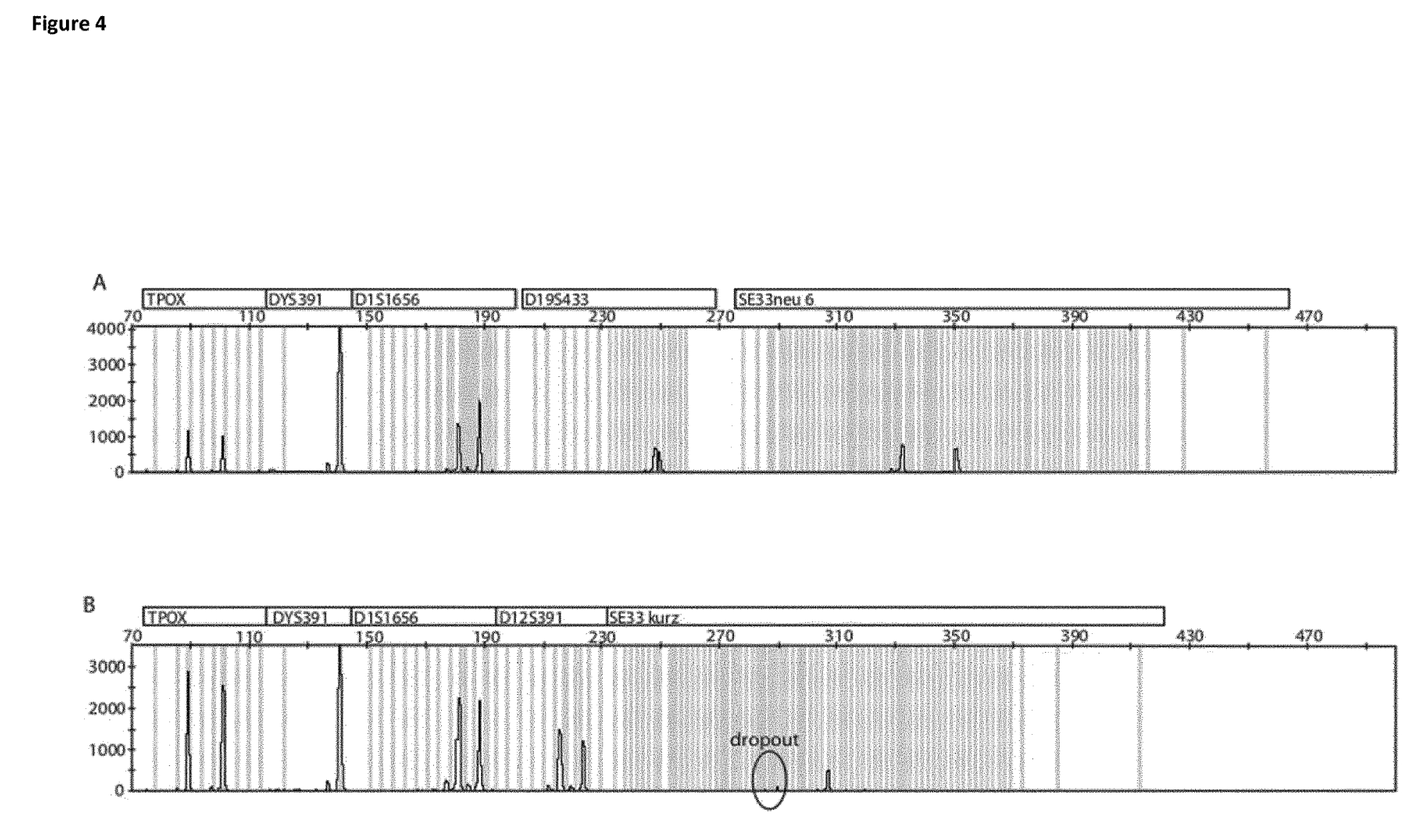

As shown in FIG. 1, several mutations in the flanking region of the target STR region were reported, that might lead to allelic dropouts or mistyping while determining the genotype of certain individuals. The primer binding site of "SE33_1_44-F" does not include any known mutations so far. Therefore, using "SE33_1_44-F//SE33_1_44-R" the amplification of SE33 proceeds with a high yield and no mistyping is detected (FIG. 4). In contrast, when using the QIAGEN "Investigator ESSplex SE Kit" (CatNo 381525) alleles are not typed correctly in all cases of DNA samples.

In addition, further DNAs were analyzed with reference to the concordance and correct genotyping of SE33. The results of the concordance analysis of "SE33_1_44-F" vs. "Investigator ESSplex SE Kit" are shown in Table 2. All DNAs were genotyped correctly with "SE33_1_44", but all DNAs showed dropouts or dropdowns when using the "Investigator ESSplex SE Kit".

TABLE 2

Concordance analysis with 2 different SE33 primers.

| | Reference | Primer | |
|---|---|---|---|
| DNA | Genotype | SE33_1_44 | ESSplex SE |
| 18414 | 17/20 | 17/20 | —/20 |
| PT83880 | 13/18 | 13/18 | 13dd/18 |
| PT83882 | 15/17 | 15/17 | 15/17dd |
| Y5 | 15/19 | 15/19 | 15dd/19 |
| PT84195 | 16/17 | 16/17 | 16dd/17 |

Annotations are as follows: dd = dropdown = very weak signal, "—" = dropout = no signal detected.

Comparision of SE33_1_44 with ACTBP2

In order to test the specificity of the primer "ACTBP2_f_seq" (Heinrich et al., International Journal of legal medicine, 2004 (118), p. 361-363) (SEQ ID NO 8) and to assess its suitability for analysis of the SE33 locus in combination of other STR5, Multiplex PCR experiments were performed. A Multiplex-PCR using 23 primer pairs simultaneously, including beside others the primer "ACTBP2_f_seq" to amplify a fragment of the SE33 marker region was performed, and the results are shown in Table 1 and 2. The amplified DNA fragments were analyzed with capillary electrophoresis (CE) on an ABI 3500 instrument. As shown in Table 3 and 4, unspecific PCR products were detected in the green, yellow and purple channel. This highlights the complexity of designing an appropriate primer pair for SE33 and shows that the primer "ACTBP2_f_seq" is not applicable for the analysis of the SE33 locus in combination with other STR5. In contrast, when performing a Multiplex-PCR using 23 primer pairs simultaneously, including beside others the primer "SE33_1_44-F" (SEQ ID NO: 1) to amplify a fragment of the SE33 marker region, no unspecific products were detected, as shown in Table 5 and 6.

the number of sequence copies found within the human genome is shown, indicating the location of a repetitive element.

TABLE 3

Specific and unspecific Multiplex-PCR products using control DNA 9948 as template and primer "ACTBP2_f_seq" (D5, SEQ ID NO: 8) for the analysis of the SE33 locus.

| Dye | specific products [bp] | | | | | | | | | unspecific products [bp] | | | | |
|---|---|---|---|---|---|---|---|---|---|---|---|---|---|---|
| Blue | 77 | 80 | 99 | 115 | 171 | 179 | 267 | 351 | 355 | | | | | |
| Green | 97 | 101 | 142 | 172 | 184 | 220 | 244 | 346.1 | 358 | 187 | 206 | 300 | 301 | 354 | 449 |
| Yellow | 104 | 116 | 173 | 179 | 248 | 252 | 308 | 312 | 417 | 357 | | | | |
| Red | 96 | 100 | 175 | 187 | 333 | 340 | | | | | | | | |
| Purple | 74 | 113 | 179 | 183 | 248 | 311 | 320 | 371 | 435 | 91 | | | | |

TABLE 4

Specific and unspecific Multiplex-PCR products using DNA 45 isolated of a blood sample as template and primer "ACTBP2_f_seq" (D5, SEQ ID NO: 8) for the analysis of the SE33 locus.

| Dye | specific products [bp] | | | | | | | | | unspecific products [bp] | | | | |
|---|---|---|---|---|---|---|---|---|---|---|---|---|---|---|
| Blue | 77 | 107 | 179 | 183 | 254 | 274 | 351 | 355 | | | | | | |
| Green | 109 | 176 | 179 | 232 | 236 | 305 | 321 | | | 187 | 195 | 203 | 244 | 353 | 449 |
| Yellow | 108 | 159 | 248 | 252 | 299 | 312 | 401 | 405 | | 357 | | | | |
| Red | 96 | 108 | 163 | 171 | 321 | 333 | | | | | | | | |
| Purple | 73 | 118 | 122 | 183 | 248 | 252 | 307 | 311 | 367 | 435 | 91 | | | |

TABLE 5

Specific and unspecific Multiplex-PCR products using control DNA 9948 as template and primer "SE33_1_44-F" (SEQ ID NO: 1) for the analysis of the SE33 locus.

| Dye | specific products [bp] | | | | | | | | | unspecific products [bp] |
|---|---|---|---|---|---|---|---|---|---|---|
| Blue | 77 | 80 | 99 | 115 | 171 | 179 | 267 | 351 | 355 | — |
| Green | 97 | 101 | 142 | 172 | 184 | 220 | 244 | 359 | 371 | — |
| Yellow | 104 | 116 | 173 | 179 | 248 | 252 | 308 | 312 | 417 | — |
| Red | 96 | 100 | 175 | 187 | 333 | 340 | | | | — |
| Purple | 74 | 113 | 179 | 183 | 248 | 311 | 320 | 371 | 435 | — |

TABLE 6

Specific and unspecific Multiplex-PCR products using DNA 45 isolated of a blood sample as template and primer "SE33_1_44-F" (SEQ ID NO: 1) for the analysis of the SE33 locus.

| Dye | specific products [bp] | | | | | | | | | | unspecific products [bp] |
|---|---|---|---|---|---|---|---|---|---|---|---|
| Blue | 77 | 107 | 179 | 183 | 254 | 274 | 351 | 355 | | | — |
| Green | 109 | 176 | 179 | 232 | 236 | 316 | 332 | | | | — |
| Yellow | 108 | 159 | 248 | 252 | 299 | 312 | 401 | 405 | | | — |
| Red | 96 | 108 | 163 | 171 | 321 | 333 | | | | | — |
| Purple | 73 | 118 | 122 | 183 | 248 | 252 | 307 | 311 | 367 | 435 | — |

FIGURE CAPTIONS

FIG. 1

Overview on the genomic context of the SE33 marker on the human chromosome 6. Annotations are as follows: The chromosomal position is given on the top. The exact location of the SE33 marker is illustrated by the upper light grey bar. The position of previously used amplicon of published primers by Polymeropoulos et al. is shown thereunder in grey. The location of the amplicon formed by the herein reported primers "SE33_1_44-F//SE33_1_44-R" is shown in black. Below, all SNP and InDel loci known from the literature or public data repositories are listed with the wild type being written over the mutant allele. At the bottom

FIG. 2

Analysis of the PCR performance of 23 HuID markers. Amplification of SE33 using the primer "SE33_1_44-F//SE33_1_44-R". All markers, in particular SE33 (second channel 4th system), were amplified with a high and equal PCR yield. No unspecific products were detected.

FIG. 3

Analysis of the PCR performance of 23 markers. Amplification of SE33 using the primer pair "SE33_1_62-F//SE33_1_62-R". The signal intensity of the SE33 PCR product is less than the signal intensity of the other markers. Unspecific PCR products were detected in the first, second and third channel (encircled and marked with an X).

FIG. 4

Analysis of the PCR performance of 5 STR markers. Annotations are as follows: SE33 marker was amplified with "SE33_1_44" (A, 5$^{th}$ STR marker) and with the primers contained in the ESSplex SE kit (B). Both SE33 alleles of reference DNA "PV 35-11_EV" were amplified with the new designed primer "SE33_1_44" in concordance to the known genotype (A, 5th STR marker). In contrast, the SE33 amplification with primers of the ESSplex SE kit leads to a mistyping of the DNA, as one allele is not amplified (B, dropout, encircled).

---

The invention claimed is:

1. A method for the detection of the presence and/or level of the SE33 marker comprising the following steps:
   i. mixing a sample with two nucleic acid oligonucleotides, wherein one nucleic acid is a forward primer consisting of a sequence selected from the group of,
      a) SEQ ID NO: 1 and,
      b) a sequence that is at least 75% identical to SEQ ID NO: 1, wherein said nucleic acid that is at least 75% identical to SEQ ID NO: 1 has at least 2 terminal 3'-prime nucleotides that are identical to the 2 terminal 3'-prime nucleotides of SEQ ID NO: 1 and, wherein, said nucleic acid may also optionally be 1 to 5 nucleotides shorter or longer at its 5' end and the other is a reverse primer suitable to form an amplification product when used with said forward primer in an amplification reaction,
   ii. performing an amplification reaction and
   iii. detection of the presence and/or level of SE33.

2. A method according to claim 1, wherein the reverse primer has a sequence selected from the group of SEQ ID NO: 2, SEQ ID NO: 4, SEQ ID NO: 6 and SEQ ID NO: 7.

3. A method according to claim 1, wherein the amplification reaction is selected from the group comprising polymerase chain reaction, rolling circle amplification, strand displacement amplification, transcription-based amplification system, nucleic acid sequence based amplification (NASBA), rolling circle amplification (RCA), transcription-mediated amplification (TMA), self-sustaining sequence replication (3SR), Qβ amplification, ligase chain reaction and isothermal amplification.

4. A method according to claim 1, wherein the detection of the presence and/or level of SE33 is performed by a method selected from the group comprising capillary electrophoresis, qPCR, digital PCR, agarose gel electrophoresis and next generation sequencing.

5. A method according to claim 1, wherein the sample is genomic DNA.

6. A method according to claim 1, wherein the sample is from one of the following sources but not limited to: saliva, urine, faeces, semen, blood, blood serum, hair, skin, teeth, humerus and femur.

7. A method according to claim 1, wherein the analysis of the presence and/or level of SE33 is in the context of forensic science.

8. A method according to claim 1, wherein the presence and/or level of SE33 is analyzed in combination with other short-tandem repeat (STR) markers.

9. A method according to claim 8, wherein the analysis is performed using multiplex PCR.

10. A method according to claim 9, wherein the multiplex PCR comprises other STR markers selected from the group of D1S1656, D2S441, D2S1338, D3S1358, D5S818, D7S820, D8S1179, D10S1248, D12S391, D13S317, D16S539, D18S51, D19S433, D21S11, D22S1045, CSF1PO, FGA [FIBRA], THO1 [TC11], TPDX, vWA, DYS391 and the gender-specific Amelogenin marker.

* * * * *